(12) United States Patent
Dewals (10) Patent No.: US 8,180,449 B2
(45) Date of Patent: May 15, 2012

(54) DUAL CHAMBER PACEMAKER

(75) Inventor: Joris Dewals, Begijnendijk (BE)

(73) Assignee: St. Jude Medical AB, Jarfalla (SE)

( * ) Notice: Subject to any disclaimer, the term of this patent is extended or adjusted under 35 U.S.C. 154(b) by 409 days.

(21) Appl. No.: 12/663,327

(22) PCT Filed: Jun. 15, 2007

(86) PCT No.: PCT/SE2007/000587
§ 371 (c)(1),
(2), (4) Date: Dec. 7, 2009

(87) PCT Pub. No.: WO2008/153453
PCT Pub. Date: Dec. 18, 2008

(65) Prior Publication Data
US 2010/0174333 A1 Jul. 8, 2010

(51) Int. Cl.
*A61N 1/362* (2006.01)
(52) U.S. Cl. .......................................................... 607/9
(58) Field of Classification Search ................ 607/9, 14, 607/15, 17
See application file for complete search history.

(56) References Cited

U.S. PATENT DOCUMENTS

| 5,318,594 A | 6/1994 | Limousin et al. |
| 2004/0010292 A1 | 1/2004 | Amblard et al. |
| 2004/0143299 A1 | 7/2004 | Casavant et al. |
| 2005/0267538 A1 | 12/2005 | Kramer et al. |

FOREIGN PATENT DOCUMENTS
WO  WO 99/10044  3/1999

*Primary Examiner* — Brian T Gedeon
(74) *Attorney, Agent, or Firm* — Schiff Hardin LLP (57) ABSTRACT

An implantable medical device and a method for operating such a device to provide cardiac pacing to the heart of a patient for pacing hearts of patients suffering from periodical or intermittent atrio-ventricular blocks, for example, AV block or HIS block. A control circuit operates the device in a DDI-II mode, the DDI-II mode being an operation mode with an atrial inhibited pacing and a DDI-II mode ventricular pacing rate being lower than a predetermined base rate of a pulse circuit of the device, during periods with atrio-ventricular conduction conditions. If a block in atrio-ventricular conduction is detected and at least one first switching criterion is satisfied, the control circuit causes a switching circuit to switch from the DDI-II mode to the DDI mode and, if a block in atrio-ventricular conduction is detected and at least one second switching criterion is satisfied, the control circuit causes the switching circuit to switch from the DDI mode to the DDD mode. The control circuit is adapted to control the switching circuit to switch back to the DDI-II mode at satisfaction of a reinitiating criterion.

31 Claims, 8 Drawing Sheets

DUAL CHAMBER PACEMAKER

This application claims the benefit as the National Stage Entry under 35 U.S.C §371 of PCT/Se07/00587, filed Jun. 15, 2007, which is incorporated by reference herein in its entirety.

FIELD OF THE INVENTION

The present invention relates to implantable medical devices including pacemakers, cardioverters, and defibrillators for selectively providing cardiac pacing to the heart of a patient. In particular, the present invention relates to improved pacing strategies for pacing hearts of patients suffering from periodical or intermittent atrio-ventricular blocks, for example, AV block or HIS block.

DESCRIPTION OF THE PRIOR ART

Many patients receiving pacemaker therapy suffer from different types of block. That is, that the impulse propagation within the heart is blocked from passing through a certain part of the stimulation path system or that the conduction occurs slower than normally. The degree of the block may vary and generally there are three types or degrees of block, namely: a first degree block, a second degree block and a third degree block.

In a first degree block, the conduction will be slower than during normal conditions but all de-polarizations waves will be conducted.

In a second degree block some of the depolarization waves will be conducted while others are blocked. The pattern of the blocks may be either regular or irregular. In a type I block of the second degree, the conduction period will be gradually prolonged from one depolarization wave to the next until a depolarization wave is completely blocked. Thereafter this development cycle start again with a normal conduction period and successively prolonged conduction periods until a complete blockage arises again. This type of block is also called Wenckebach block. A type II block is a partial block in that only some of the depolarization waves are conducted according to a regular pattern. The conduction period is either normal or prolonged, but constant, in the cycles with conduction.

In a block of the third degree, no conduction at all takes place. Thus, the depolarization waves are completely blocked.

Present solutions for providing pacemaker therapy to patients suffering from temporary or intermittent atrio-ventricular blocks, e.g. AV block or HIS block, include a mode switch from an AAI mode to a DDD mode when block is detected or AV hysteresis, i.e. an AV interval is successively increased if an intrinsic ventricular event is detected and is returned to an initial duration at a paced ventricular event.

In such a case, if the pacemaker's AV interval is not properly programmed, the pacemaker will deliver an unneeded and undesirable ventricular pacing pulse. A ventricular pacing at a period without atrio-ventricular block, may cause competition between the paced and spontaneous de-polarizations, and pacing consumes added energy for such unneeded pulses which shortens the useful life of an implanted, battery-operated pacemaker.

Furthermore, several studies have demonstrated the disadvantageous short-term hemodynamic effects of inappropriate ventricular pacing, which also may prove harmful when allowed to continue for an extended period of time. In addition, recent studies have shown the drawbacks of continuous right ventricular pacing.

Therefore, significant efforts have been made to reduce or limit the amount of ventricular pacing in patients having sick hearts and suffering from periodical or intermittent atrio-ventricular blocks.

In U.S. Pat. No. 5,318,594 discloses a cardiac pacemaker of the DDD type that operates in the DDD mode solely during periods of crisis, i.e. during periods of AV block, and that operates in the AAI mode outside the periods of crisis. The heart is paced in the AAI mode during atrio-ventricular conduction periods and in a response to lack of atrio-ventricular conduction the pacing is automatically switched to the DDD mode. When the atrio-ventricular conduction is restored, the pacing is automatically switched back to the AAI mode.

WO 99/10044 describes a pacemaker that is capable of switching from one mode of pacemaker function, an atrial pacemaker function such as AAI pacing, to another mode of pacemaker function, a venticular pacemaker function such as DDD function or VVI function. The switching between the modes takes place in response to an empirically determined VV interval between heartbeats in the ventricles of the heart of the patient. The VV intervals are set to be long, preferably above 2000 ms.

Furthermore, in U.S. Application Publication No. 2004/0143299 a pacing system for continuously monitoring ventricular response is disclosed. The pacemaker checks, in an ADI mode, on a beat-to-beat basis for intact AV conduction and will continue to pace the atrium and allow the conducted ventricular event to take place. If intermittent AV block occur, the mode automatically switches to the DDI mode for one cycle and then to the DDD mode for one or as many cycles as necessary and upon the detection of the presence of AV conduction, the mode switches back to the ADI mode.

However, the pacing strategies described in the prior art are not optimal with respect to the degree of ventricular pacing and the level of patient comfort and there is a need within the art of a pacing strategy that minimizes the degree of ventricular pacing without causing unnecessary discomfort to the patient. Moreover, the prior art methods are not optimal with respect to energy consumption since unneeded ventricular pulses shortens the useful life of an implanted, battery-operated pacemaker.

SUMMARY OF THE INVENTION

Thus, an object of the present invention is to provide an implantable medical device and a method for operating such a device that is capable of minimizing ventricular pacing in hearts of patients suffering from intermittent atrio-ventricular blocks, for example, AV block or HIS block without causing unnecessary discomfort to the patient.

A further object of the present invention is to provide an implantable medical device and a method for operating such a device that automatically adapts a pacing mode of the device to changing hemodynamics and changing physiological conditions of the patient.

Still another object of the present invention is to provide a more energy efficient implantable medical device and a method for operating such a device in an energy efficient manner.

In order to clarify, the letters defining the features of the different operation modes are, for the person familiar with the state of the art, the well-known NBG code.

For clarity, the term DDI-II mode refers to an operation mode with an atrial inhibited pacing and a ventricular pacing at a rate being lower than a predetermined base rate of the implantable device, wherein the base rate is the rate at which the pulse generator generates paces in the absence of intrinsic activity, expressed in pulses per minute (bpm).

In the context of the present application, the term atrial event refers to a paced atrial depolarization, an A-wave, or an intrinsic atrial event, a P-wave, and the term ventricular event refers to a paced ventricular depolarization, a V-wave, or to an intrinsic ventricular depolarization, i.e. a R-wave, respectively.

The above object is achieved in accordance with the present invention by an implantable medical device (IMD) that includes a pacing pulse circuit connectable to cardiac leads to deliver cardiac pulses to cardiac tissue via the cardiac leads, a monitoring circuit that monitors atrial and/or ventricular events, so that atrio-ventricular conduction conditions can be detected, and a switching circuit that switches between operation modes of the IMD, including a DDI-II mode, a DDI mode, and a DDD mode, the DDI-II mode being an operation mode with an atrial inhibited pacing and a DDI-II mode ventricular pacing rate that is lower than a predetermined base rate of the IMD, the DDI mode being an operation mode with a synchronized atrial and ventricular pacing. The IMD also has a control circuit that is configured to operate the IMD in the DDI-II mode during periods with atrial-ventricular conditions, and, if a block in atrio-ventricular conduction is detected and at least one first switching criterion is satisfied during operation in the DDI-II mode, to control the switching circuit to switch from the DDI-II mode to the DDI mode, and, if a block in atrio-ventricular conduction is detected and at least one second switching criterion is satisfied during operation in the DDI mode, to control the switching circuit to switch from the DDI mode to the DDD mode. Furthermore, the control circuit is configured to, during operation in the DDD mode, control the switching circuit to switch back to the DDI-II mode upon satisfaction of a reinitiating criterion.

The above object also is achieved in accordance with the invention a method for an implantable medical device (IMD) for selectively providing cardiac pacing to a heart of a patient. The method includes delivering cardiac pacing pulses to cardiac tissue; detecting atrio-ventricular conduction by monitoring atrial and/or ventricular events; switching between operation modes of the implantable medical device including a DDI-II mode, a DDI mode and a DDD mode, the DDI-II mode being an operation mode with an atrial inhibited pacing and a DDI-II mode ventricular pacing rate being lower than a predetermined base rate of the pulse circuit; operating the device in the DDI-II mode during periods with atrio-ventricular conduction conditions; if a block in atrio-ventricular conduction is detected and at least one first switching criterion is satisfied during operation in the DDI-II mode, switching the DDI-II mode to the DDI mode; if a block in atrio-ventricular conduction is detected and at least one second switching criterion is satisfied during operation in the DDI mode, switching the DDI mode to the DDD mode; and, at satisfaction of at least one re-initiating criterion, switching the DDD mode back to the DDI-II mode.

The invention also encompasses a computer-readable medium encoded with programming instructions, the medium being loadable into an internal memory of an implantable medical device and the programming instructions causing a processor, having access to the internal memory, to operate the implantable medical device according to the method in accordance with the invention described above.

Thus, the present invention is based on the idea of, at detection of a conduction block, providing a prolonged block detection period to allow more time for the intrinsic conduction to re-establish at the same time as a support cardiac output is provided during the detection period. The period during which the device is in the DDD mode can thereby be reduced. This together will result in a lower degree of ventricular pacing at the same time as a reasonable patient comfort is maintained. Consequently, the patient can be protected at the same time as AV node conduction is encouraged.

This provides several advantages in comparison to the prior art. For example, in the device shown in U.S. Pat. No. 5,318,594, the pacing is automatically switched to the DDD mode in a response to lack of atrio-ventricular conduction from the AAI mode. Accordingly, the switching takes place directly upon the detection of a block and the intrinsic conduction is not given any time to re-establish before the DDD mode is activated. When operating in the DDD mode it may be difficult to re-establish the intrinsic conduction.

Furthermore, in the device shown in WO 99/100442, the switching between the AAI mode and the DDD mode takes place in response to a programmed long VV interval, preferably above 2000 ms, between heartbeats in the ventricles of the heart of the patient. The long VV interval may cause unnecessary discomfort to the patient due to the fact that it may occur long periods without any ventricular event before the switching takes place.

In the device described in U.S. Application Publication No. 2004/0143299, if intermittent AV block occur, the mode automatically switches to the DDI mode from an ADI mode, i.e. on a beat-to-beat basis for intact AV conduction and will continue to pace the atrium and allow the conducted ventricular event to take place, for one cycle and then to the DDD mode for one or as many cycles as necessary. Accordingly, the switching to the DDI mode takes place directly upon the detection of a block and the switching to the DDD mode takes place after one cycle in the DDI mode. Thereby, the intrinsic conduction is not given enough time to re-establish before the DDD mode is activated.

According to an embodiment of the present invention, the control circuit is adapted to, when the device is operated in the DDI-II mode, at each detected intrinsic ventricular event or paced ventricular event, control the pacing pulse circuit to adapt a ventricular interval according to predetermined rules depending on at least one preceding ventricular event, e.g. the ventricular interval may be adapted differently depending on whether a preceding event was or the preceding events were intrinsic or paced or a combination thereof. Thus, the support cardiac output is adjusted during the DDI-II mode in order to extend the period of time during which the intrinsic conduction is given an opportunity to re-establish at the same time as a reasonable patient comfort is provided.

In one embodiment of the present invention, the predetermined rules are the following: at each paced ventricular event, the pacing pulse circuit is controlled to reduce or shorten a present ventricular interval with a first predetermined percentage; and at sensing of at least two consecutive intrinsic ventricular events, the pacing pulse circuit is controlled to increase or prolong the present ventricular interval with a second predetermined percentage.

In a particular example, the first predetermined percentage is twice the second predetermined percentage. Thereby, it is possible to obtain a compromise between giving the intrinsic conduction an opportunity to re-establish and providing a reasonable patient comfort. During a long period of atrio-ventricular non-conduction, the ventricular pacing interval will gradually be reduced and the patient comfort is hence gradually improved.

In a further alternative, wherein the predetermined rules are the following: at each paced ventricular event, the pacing pulse circuit is controlled to decrease or shorten a present ventricular interval with a first predetermined percentage in relation to an initial ventricular interval; and at sensing of at least two consecutive intrinsic ventricular events, the pacing pulse circuit is controlled to increase or prolong the present ventricular interval with a second predetermined percentage in relation to the initial ventricular interval; and wherein the initial ventricular interval is the DDI-II mode ventricular interval. The operation mode is switched to the DDI mode when ventricular pacing interval is equal to the atrial pacing interval.

According to another embodiment of the present invention, the at least one first switching criterion is that no atrio-ventricular conduction has been detected during a predetermined first period having a duration of at least two cardiac cycles and that a ventricular interval is at least equal to an atrial interval. Thereby, the period during which the device is operated in DDI-II mode can be prolonged in that there is, in principle, a gradual transition from the DDI-II mode to the DDI mode. The gradual transition given the intrinsic conduction a fair opportunity to re-establish at the same time as a reasonable patient comfort is provided.

In embodiments of the present invention, atrio-ventricular conduction is defined as periods with consecutive intrinsic ventricular events which may be interrupted by a paced ventricular event. Alternatively, the interruption may be allowed to last for a predetermined period of time. Consequently, it is checked whether an interruption in the atrio-ventricular conduction is of a temporary nature or whether it is of a more permanent nature in that a short interruption in a period of functioning atrio-ventricular conduction not will lead to a mode switch. Thus, the intrinsic conduction is given an opportunity to re-establish before a mode switch from the DDI-II mode to the DDI mode is executed.

In one embodiment of the present invention, the at least one second switching criterion is that ventricular pacing pulses has been delivered for a period having a predetermined length of time. According to another embodiment of the present invention, the at least first switching criterion is that no atrio-ventricular conduction has been detected during a predetermined first period having a duration of at least two cardiac cycles.

According to a further embodiment of the present invention, the control circuit is adapted to, when the device operates in the DDI mode, control the switching circuit to switch back to the DDI-II mode if at least one re-initiation criterion for the DDI mode is satisfied. For example, the at least one re-initiation criterion for the DDI mode may be that atrio-ventricular conduction is restored for a period being longer than a predetermined period of time or that a predetermined number of consecutive intrinsic ventricular events have been detected.

In yet another embodiment of the present invention, the reinitiating criterion in the DDD mode is that atrio-ventricular conduction is restored for a period having a duration of a predetermined number of cardiac cycles.

In accordance with a further embodiment of the present invention, the control circuit is adapted to, when the device operates in the DDD mode, regularly search for intrinsic ventricular activity. In one embodiment, this is performed by, at predetermined intervals, increase an AV interval during a period of time having a length of a predetermined number of cycles. During the regular DDD operation, it is difficult for the intrinsic conduction to re-establish and by increasing the AV interval during limited periods of time the intrinsic conduction is given an improved opportunity to re-establish without causing to much discomfort to the patient during this limited periods of time. That is, it is provided for a possibility for ventricular inhibition.

As realized by the person skilled in the art, steps of the methods of the present invention, as well as preferred embodiment thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

In the following, the present invention will be discussed in the context of a pacemaker of dual chamber type.

Figure 1:
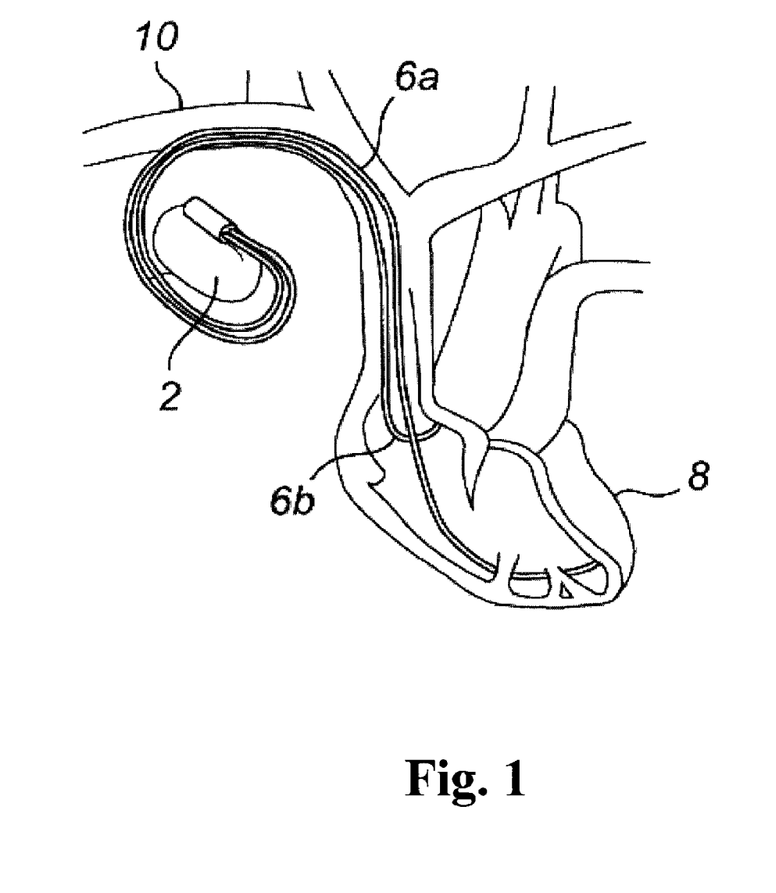
FIG. 1 schematically shows an embodiment of a pacemaker system in which an implantable medical device in accordance with the present invention may be implemented.

With reference first to FIG. 1, there is shown a schematic diagram of a dual chamber pacemaker implanted in a patient in the present invention can be implemented. The pacemaker 2 comprises a housing being hermetically sealed and biological inert. Normally, the housing is conductive and may thus serve as an electrode. Two pacemaker leads are electrically coupled to the pacemaker 2 in conventional manner, namely a right ventricular lead 6a and an atrial lead 6b. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As the skilled man in the art realizes, the leads 6a, 6b may be implanted with its distal end located in either the atrium or ventricle of the heart 8. The pacemaker leads are normally implanted via a jugular or cephalic vein to vena cava superior and the right atrium and right ventricle.

Although the present invention will be described herein in one embodiment which includes a pacemaker those of ordinary skill in the art will appreciate that present invention may be advantageously practiced in connection with numerous other types of implantable medical device and systems, for example, in cardioverters or defibrillators.

Figure 2:
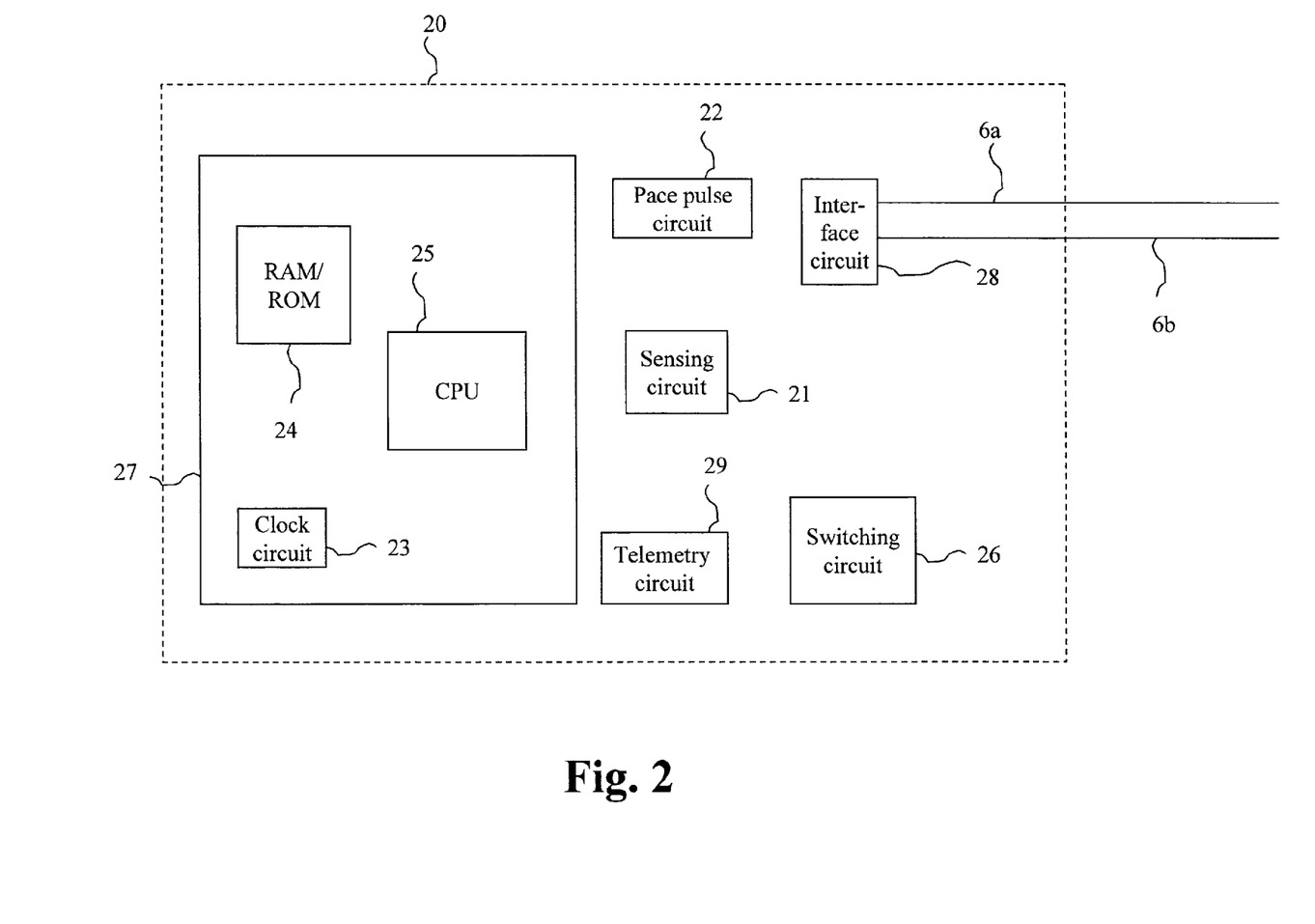
FIG. 2 schematically illustrates an embodiment of the implantable medical device according to the present invention.

FIG. 2 is block diagram of the electronic circuitry and components of the implantable medical device in accordance with the present invention. To the extent that certain components of the pacemaker 20, e.g. the pacemaker shown in FIG. 1, are conventional to their design and operation, such components will not be described herein in detail. For example, the pacemaker 20 comprises a stimulation control circuit 27 for controlling the pacing and sensing functions of the device. The control circuit 27 controls, inter alia, pace pulse parameters such as output voltage and pulse duration. The control circuit 27 includes circuits well-known in the art, for example, a RAM/ROM unit (random-access and read-only memory) 24, a crystal clock 23, and a central processing unit (CPU) 25. The pacemaker further includes circuits well-known in the art, for example, a sensing circuit 21, and a pace pulse circuit 22.

Furthermore, the pacemaker 20 includes a communication unit 29 adapted to communicate with an external programmer/control unit (not shown).

The pacemaker 20 is connectable to pacemaker leads 6a, a right ventricular lead, and 6b, right atrium lead, respectively, for delivering signals between the pacemaker 20 and tissue of the heart. The leads 6a, and 6b may be unipolar or bipolar, and may include any of the passive or active fixation means known in the art for fixation of the lead to the cardiac tissue. As an example, the lead distal tip (not shown) may include a tined tip or a fixation helix. The leads 6a and 6b comprises one or more electrodes such tip electrodes, ring electrodes, coil electrodes, arranged to, inter alia, transmit pacing pulses for causing depolarization of cardiac tissue adjacent to the electrode(-s) generated by a pace pulse circuit 22 under influence of the control circuit 27. The coupling of conductors of the leads 6a and 6b and internal components of the pacemaker 20 may be by means of an interface circuit 28 which functions, in a multiplexer-like manner, to selectively and dynamically establish necessary connections between various conductors of the leads 6a and 6b and the components of the pacemaker as familiar to the man skilled within the art.

Although specific connection between the CPU 25 and other components of the control circuit 27 and other components of the pacemaker 20 are not shown in FIG. 2, it will be apparent to those of ordinary skilled in the art that the CPU 25 functions to control the timed operation of the pace pulse circuit 22 and the sensing circuit 21 under control of programming stored in the RAM/ROM unit 24. The clock circuit 23, for example, a crystal controlled oscillator provides main timing clock signals to the pace pulse circuit 22. For the sake of clarity, the lines over which such signals are transmitted to the various times circuits (e.g. the CPU 25) are omitted in FIG. 2.

Furthermore, the components of the pacemaker 20 are powered by a battery (not shown) in accordance with common practice within the art.

The sensing circuit 21, which is of conventional design, is adapted to receive electrical cardiac signals from the leads 6a and 6b and to process such signals to detect the occurrence of specific cardiac events, for example, atrial contractions (P-waves) and ventricular contractions (R-waves). The sensing circuit may provide event-indicating signals, e.g. signals indicating the detected event including atrial contractions (P-waves) and ventricular contractions (R-waves), which may be used by the CPU 25 to control the synchronous stimulating operations of the pacemaker 20 in accordance with common practice within the art.

The pacemaker 20 further comprises a switching circuit 26 adapted to switch between operation modes including a DDI-II mode, a DDI mode and a DDD mode. The letters defining the features of the operation modes are, for the person familiar with the state of the art, the well-known NBG code.

The DDI-II mode is an operation mode with an atrial inhibited pacing and a DDI-II mode ventricular pacing set at percentage of the atrial rate, at a predetermined rate which is lower than the base rate. Intrinsic atrial activity during the alert period will inhibit the output pulse and reset the pacemaker timing to the beginning of the refractory period. The ventricular pacing thus functions as a back-up pacing in case the atrio-ventricular conduction is temporary blocked. The ventricular timer function will operate at an interval which is extended to a percentage of the atrial timer. For example, the atrial rate may be set to 60 Bpm, and the atrial timer is thus set to 1000 ms. The ventricular timer may be set to 140% of the atrial, the ventricular timer is thus set to 1400 ms or 42 Bpm.

The DDI mode refers to dual-chamber, non-tracking pacing, with sensing in both chambers. Pacing and sensing occur in both the atrium and ventricle with inhibited response. The synchronized atrial and ventricular pacing, i.e. sensing and stimulation can be effected in both in atrium and ventricle, in accordance with common practice within the art. An A-V interval timer can be reset by an expired atrial escape interval (atrial pacing is delivered if no inhibition has occurred) and a sensed spontaneous ventricle event outside the A-V interval. In the absence of ventricular activity, a ventricular output pulse will be provided at the end of the programmed rate (V-V) interval. AV sequential pacing at the programmed rate is provided in the absence of intrinsic activity. Additionally, intrinsic ventricular activity occurring during the ventricular alter period of the atrial escape interval or AV delay will thus inhibit the pacemaker and reset the timing The DDD mode refers to dual-chamber pacing with atrial tracking, i.e. pacing and sensing in both atrium and ventricle with dual response (inhibited or triggered) to sensing. In the absence of intrinsic activity, both chambers are paced at a programmed base rate and AV delay. Atrial and ventricular events are sensed and stimulation can be delivered in both atrium and ventricle in accordance with common practice within the art. An A-V interval timer can be reset by a sensed atrial event, an expired atrial escape interval and a sensed spontaneous ventricle event outside the A-V interval. When an intrinsic atrial event is sensed during the atrial alert interval, the atrial output pulse is inhibited and the timing cycle for the PV delay begins. If no intrinsic atrial event is sensed, an atrial pulse is delivered at the end of the atrial alert interval and the timing cycle for the AV delay beings. In the presence of atrial pacing, rate acceleration does not occur if an intrinsic ventricular event is sensed during the AV/PV delay, although ventricular output is inhibited. If no ventricular event is sensed in AV/PV delay, it times out, a ventricular pulse is delivered, and the timing cycle for the atrial escape interval begins. Intrinsic ventricular activity sensed during the ventricular alert period will inhibit both atrial and ventricular output pulses and recycle the timing cycles on both channels to the beginning of the atrial alert interval.

Moreover, the pacemaker 20 may comprise other components and circuits, for example, activity sensors in addition to the components and circuits described above.

Figure 3:
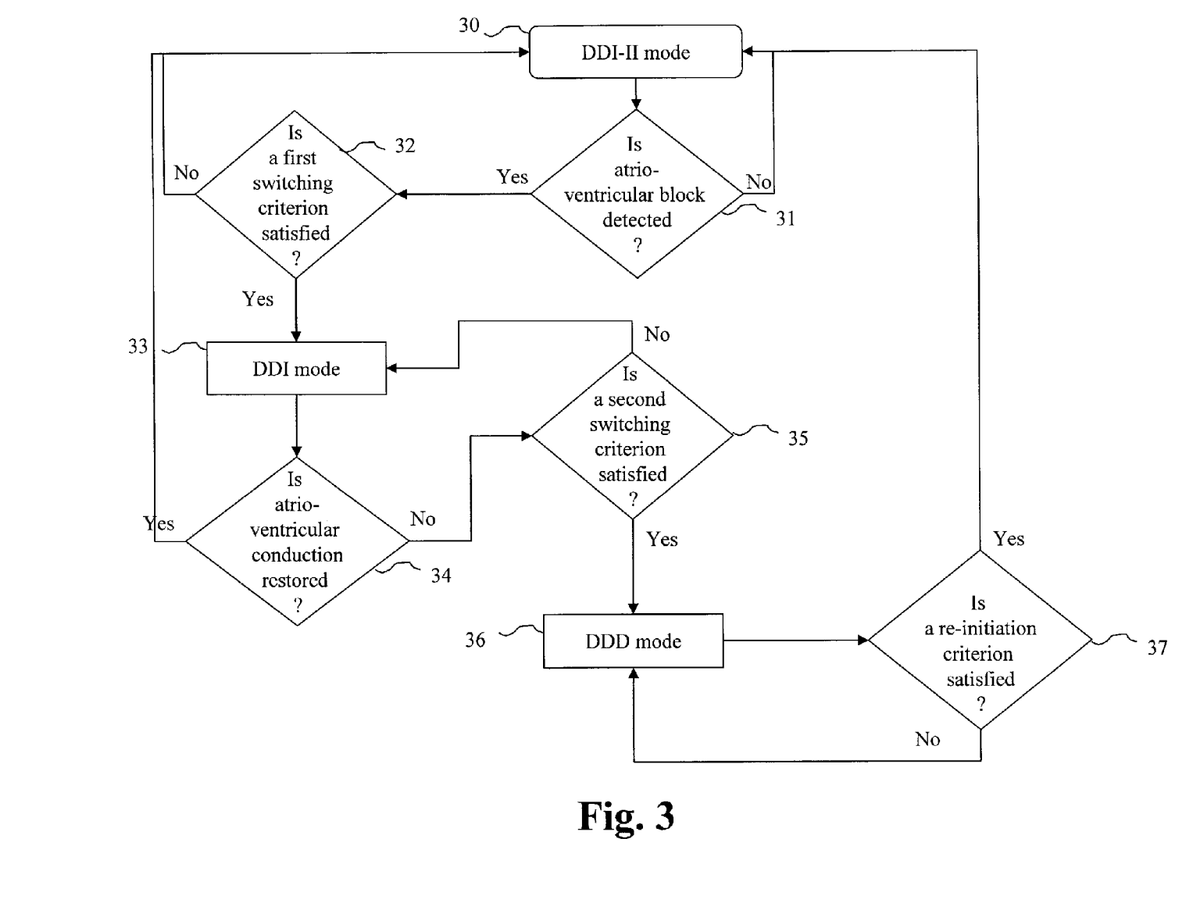
FIG. 3 is a high-level flow chart of an embodiment of the method for selectively providing cardiac pacing to a heart of a patient according to the present invention.

Referring to FIG. 3, a high-level flow chart illustrating an embodiment of the method for selectively providing cardiac pacing to a heart of a patient according to the present invention will be discussed. First, at step 30, during periods without crisis, i.e. during periods with detected atrio-ventricular conduction, the pacemaker is operated in the DDI-II mode. It is continuously checked, in step 31, whether atrio-ventricular block is detected and if a block is detected the procedure proceeds to step 32.

At step 32, a check whether at least one first switching criterion is satisfied or whether at least a first switching event has been detected or occurred is performed. According to one embodiment, the at least one first switching criterion is that no intrinsic ventricular event has been detected during a period of at least two consecutive cardiac cycles, i.e. the ventricle has been paced with the predetermined DDI-II mode ventricular rate during two consecutive cycles. If the at least one first criterion is not satisfied, i.e. the atrio-ventricular conduction is restored within the period of time defined by the first switching criterion, the procedure returns to step 30. On the other hand, if the criterions is found to be satisfied, the procedure proceeds to step 33 where a mode switch from the DDI-II mode to the DDI mode is executed. In one embodiment, the ventricular pacing rate of the DDI-II mode is used in the DDI mode as an initial ventricular pacing rate.

At step 34, a check is regularly performed whether the atrio-ventricular conduction has been restored, i.e. whether an intrinsic ventricular event is sensed in the next cardiac cycle, for example, in each cycle. It may also be checked whether the restored conduction is temporary or not. That is, if the conduction is restored for a period of time being longer than a predetermined period. For example, if at least a predetermined number of successive or consecutive intrinsic ventricular events are detected, i.e. a predetermined number of consecutive inhibitions. If the atrio-ventricular conduction has been restored (and is determined not to be only temporary), the procedure returns to step 30, i.e. the operation mode switches back to the DDI-II mode.

On the other hand, if no, e.g. if only one intrinsic ventricular event was sensed and a subsequent ventricular event was a paced event the procedure proceeds to step 35 where it is checked whether at least one second switching criterion is satisfied or whether at least a first switching event has been detected or occurred is performed. According to one embodiment, the at least one second switching criterion is that a number of consecutive ventricular pacing pulses have been delivered. If yes, the procedure proceeds to step 36 where the operation mode is switched from the DDI mode to the DDD mode. On the other hand, if no, the procedure returns to step 33 and hence the operation is maintained in the DDI mode.

Figure 5:
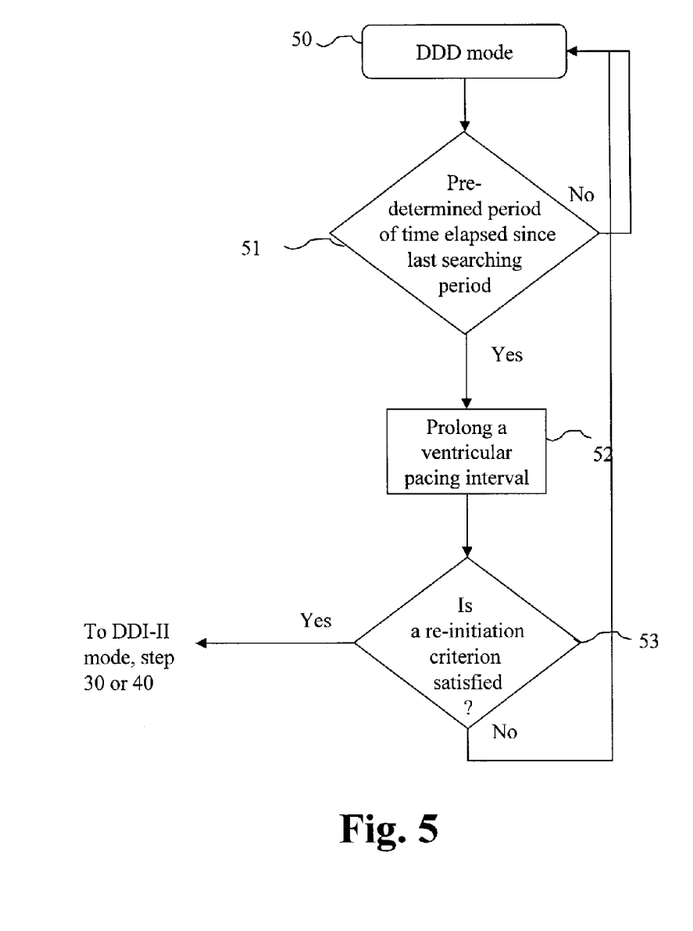
FIG. 5 is a flow chart of an embodiment for searching for AV conduction in the DDD mode.

At step 37, it is continuously checked whether at least one re-initiation criterion is satisfied, wherein one embodiment is illustrated in detail in FIG. 5. In this embodiment, at step 51, the ventricular rate is adapted to regularly search for R-waves. Thus, at regular intervals, a searching period is, at step 52, initiated in which a present ventricular pacing interval is prolonged during a period of time having a length of a predetermined number of cycles. For example, after a predetermined period of time, the ventricular pacing interval is prolonged, for a predetermined number of cycles, e.g. the ventricular interval may be set to 140% of the present ventricular interval, the search period may have a length of 5 cycles, and the search may be performed at intervals of 8000 ms. During the regular DDD operation, it is difficult for the intrinsic conduction to re-establish and by significantly decreasing the ventricular pacing rate during limited periods of time the intrinsic conduction is given an improved opportunity to re-establish without causing to much discomfort to the patient during this limited periods of time. If the at least one re-initiation criterion for the DDI-II mode is satisfied, see step 53 in FIG. 5, a mode switch back to the DDI-II mode is performed, i.e. with reference to FIG. 3 the procedure returns to step 30. For example, the at least one re-initiation criterion for the DDI-II mode may be that atrio-ventricular conduction is restored for a period being longer than a predetermined period of time or that a predetermined number of consecutive intrinsic ventricular events have been detected, i.e. the a predetermined number of consecutive inhibitions have occurred. In yet another embodiment of the present invention, the reinitiating criterion in the DDD mode is that atrio-ventricular conduction is restored for a period having a duration of a predetermined number of cardiac cycles, i.e. the intrinsic ventricular events are detected or sensed during a predetermined number of consecutive cycles. In accordance with a further embodiment of the present invention, the control circuit is adapted to, when the device operates in the DDD mode, regularly search for intrinsic ventricular activity.

Figure 4:
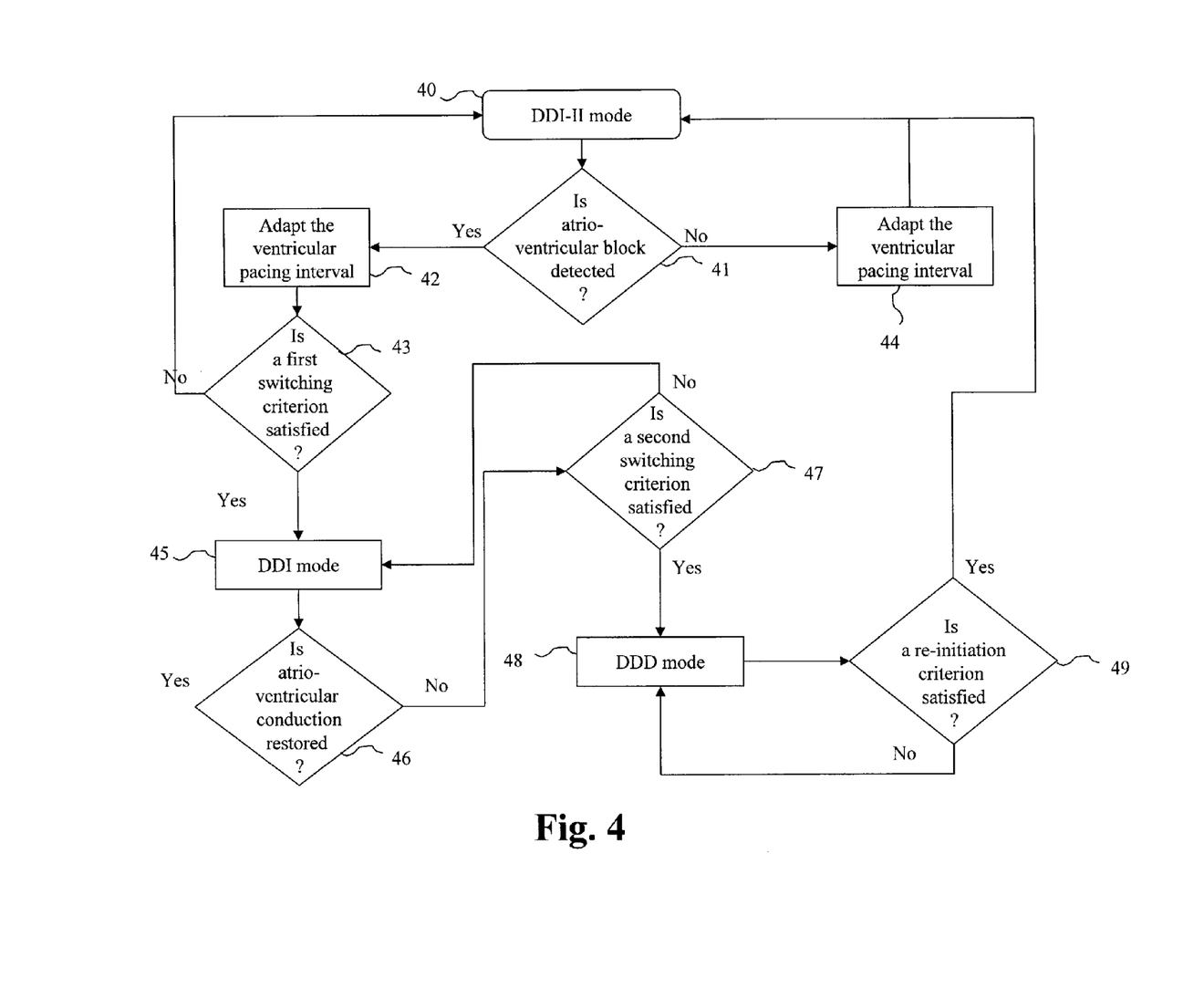
FIG. 4 s a high-level flow chart of a further embodiment of the method for selectively providing cardiac pacing to a heart of a patient according to the present invention.

Turning now to FIG. 4 a high-level flow chart illustrating a further embodiment of the method for selectively providing cardiac pacing to a heart of a patient according to the present invention will be discussed. First, at step 40, during periods without crisis, i.e. during periods with detected atrio-ventricular conduction, the pacemaker is operated in the DDI-II mode. It is continuously checked, i.e. in each cycle, in step 41, whether atrio-ventricular block is detected and if a block is detected, i.e. a ventricular pace is delivered when the ventricular DDI-II mode interval has timed out (the prolonged initial interval set to a predetermined percentage of the base rate, for example, 140%). If yes, the procedure proceeds to step 42. Then, at step 42, the ventricular DDI-II mode interval is adapted according to predetermined rules depending on at least one preceding ventricular event. In one embodiment, it is shortened with a predetermined percentage w % at each paced ventricular event. In one embodiment, the predetermined percentage is 10%. Thereafter, at step 43, it is checked whether at least one first switching criterions is satisfied. In this embodiment, the at least one first switching criterion is that the ventricular pacing interval is equal to the atrial interval. If no, the procedure returns to step 40. If an intrinsic event is detected, i.e. the atrio-ventricular conduction functions, the ventricular pacing interval is adapted in step 44 according to predetermined rules depending on at least one preceding ventricular event. In this embodiment, the ventricular pacing interval is prolonged a predetermined percentage w/2% for each intrinsic event and in another embodiment the interval is prolonged w/2% for each two consecutive intrinsic ventricular events. The maximum length is the initial length of the interval, i.e. prolonged initial interval set to a predetermined percentage of the base rate, for example, 140%. Subsequently, the procedure returns to step 40.

However, if yes in step 43, i.e. the ventricular pacing interval is equal to the atrial interval, the procedure proceeds to step 45 where a mode switch is executed and the operation mode is switched from the DDI-II mode to the DDI mode.

At step 46, a check is regularly performed whether the atrio-ventricular conduction has been restored, i.e. whether an intrinsic ventricular event is sensed in the next cardiac cycle, for example, in each cycle. It may also be checked whether the restored conduction is temporary or not. That is, if the conduction is restored for a period of time being longer than a predetermined period. For example, at least a predetermined number of successive or consecutive intrinsic ventricular events are detected, i.e. a predetermined number of consecutive inhibitions. If the atrio-ventricular conduction has been restored (and is determined not to be only temporary), the procedure returns to step 40, i.e. the operation mode switches back to the DDI-II mode from the DDI mode.

On the other hand, if no, e.g. only one intrinsic ventricular event was sensed and a subsequent ventricular event was a paced event, the procedure proceeds to step 47 where it is checked whether at least one second switching criterion is satisfied or whether at least a first switching event has been detected or occurred is performed. According to one embodiment, the at least one second switching criterion is that a number of consecutive ventricular pacing pulses have been delivered. If yes, the procedure proceeds to step 48 where the operation mode is switched from the DDI mode to the DDD mode. On the other hand, if no, the procedure returns to step 45 and hence the operation is maintained in the DDI mode.

At step 49, it is continuously checked whether at least one re-initiation criterion is satisfied, wherein one embodiment is illustrated in detail in FIG. 5. In this embodiment, at step 51, the ventricular rate is adapted to regularly search for R-waves. Thus, at regular intervals, a searching period is, at step 52, initiated in which a present ventricular pacing interval is prolonged during a period of time having a length of a predetermined number of cycles. For example, after a predetermined period of time, the ventricular pacing interval is prolonged, for a predetermined number of cycles, e.g. the ventricular interval may be set to 140% of the present ventricular interval, the search period may have a length of 5 cycles, and the search may be performed at intervals of 8000 ms. During the regular DDD operation, it is difficult for the intrinsic conduction to re-establish and by significantly decreasing the ventricular pacing rate during limited periods of time the intrinsic conduction is given an improved opportunity to re-establish without causing to much discomfort to the patient during this limited periods of time. If the at least one re-initiation criterion for the DDI-II mode is satisfied, see step 53 in FIG. 5, a mode switch back to the DDI-II mode is performed, i.e. with reference to FIG. 4 the procedure returns to step 40. For example, the at least one re-initiation criterion for the DDI-II mode may be that atrio-ventricular conduction is restored for a period being longer than a predetermined period of time or that a predetermined number of consecutive intrinsic ventricular events have been detected, i.e. the a predetermined number of consecutive inhibitions have occurred. In yet another embodiment of the present invention, the reinitiating criterion in the DDD mode is that atrio-ventricular conduction is restored for a period having a duration of a predetermined number of cardiac cycles, i.e. the intrinsic ventricular events are detected or sensed during a predetermined number of consecutive cycles. In accordance with a further embodiment of the present invention, the control circuit is adapted to, when the device operates in the DDD mode, regularly search for intrinsic ventricular activity.

Figure 6:
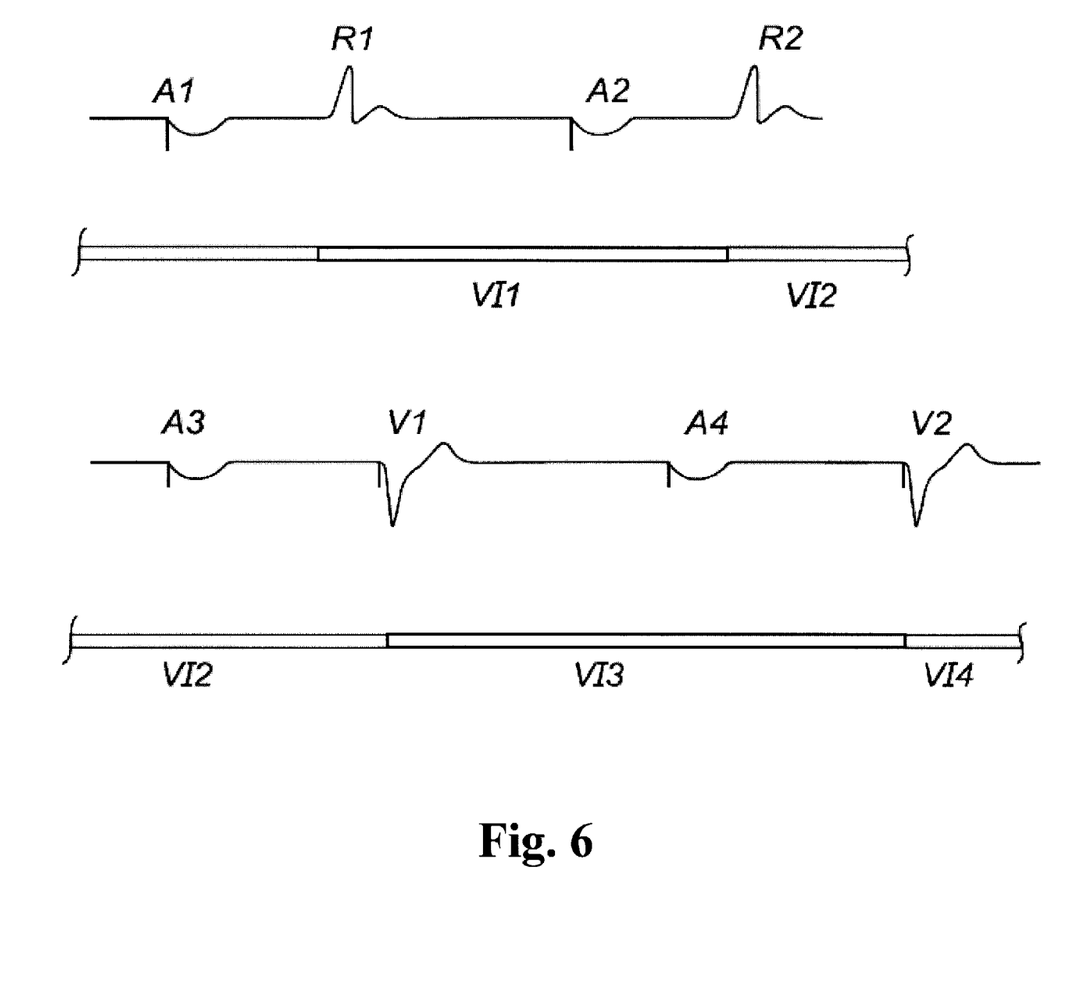
FIG. 6 is a diagram illustrating an example of the cardiac activity and operation of the device during the DDI-II mode.

With reference now to FIG. 6, an example of the operation in the DDI-II mode according to the present invention will be discussed.

As discussed above, the DDI-II mode is an operation mode with an atrial inhibited pacing and a DDI-II mode ventricular pacing rate which is set at percentage of the atrial rate, i.e. at a predetermined rate which is lower than the base rate. The ventricular pacing thus functions as a back-up pacing. The ventricular timer function will operate at an interval which is extended to a percentage of the atrial timer. For example, the atrial rate may be set to 60 Bpm, and the atrial timer is thus set to 1000 ms. The ventricular timer may be set to 140% of the atrial and the ventricular timer is thus set to 1400 ms or 42 Bpm.

During periods with detected atrio-ventricular conduction, i.e. periods with atrial events, paced or intrinsic, followed by intrinsic ventricular events, the pacemaker 20 is operated in the DDI-II mode. A paced artial event A1 triggers an atrial refractory interval and the intrinsic ventricular event R1 triggers a ventricular refractory period and a ventricular DDI-II mode interval VI1, which is extended in comparison to the base interval. Thus, the atrial-ventricular conduction functions. According to embodiments, the ventricular DDI-II mode interval is set to 140% of the base interval. Hence, if a ventricular DDI-II mode interval VIx, expires without the detection of an intrinsic ventricular event, i.e. a R wave, a paced ventricular event will be evoked by delivering a ventricular pacing pulse.

Further, the paced atrial event A2 triggers an atrial refractory interval. An intrinsic ventricular event R2 is detected within the ventricular DDI-II mode interval VI1, hence resetting the ventricular DDI-II mode interval VI1 and initiating a new ventricular DDI-II mode interval VI2. The ventricular interval is maintained at the initial length since the initial length was used as timing interval. If it had been shorter than the initial length, due to the delivery of ventricular pacing, the ventricular interval had been prolonged w/2%, for example, 5%. A paced atrial event A3 triggers an atrial refractory interval. In this case, the ventricular DDI-II mode interval VI2 expires without the detection of an intrinsic ventricular event or R wave. Synchronized with the point of time at which the ventricular DDI-II mode interval expires, a stimulation pulse for evoking a stimulation pulse is delivered evoking a ventricular event, which is indicated in FIG. 6 with V1. The ventricular interval is also shortened with w %, for example 10%, for each paced ventricular event according to this embodiment. Thereby, a gradual increase of the DDI-II mode ventricular rate can be achieved and an abrupt switch from the DDI-II mode to the DDI mode can thus be avoided. The paced ventricular event V1 triggers a ventricular refractory interval and a new ventricular DDI-II mode interval VI3. A paced atrial event A4 triggers an atrial refractory interval. In this exemplifying case, also the ventricular DDI-II mode interval VI3 expires without the detection of an intrinsic ventricular event. Synchronized with the point of time at which the ventricular DDI-II mode interval VI3 expires, a stimulation pulse for evoking a ventricular event is delivered, which event is indicated in FIG. 6 with V2. The ventricular interval is again shortened with w %.

According to an embodiment of the present invention, the mode switch from the DDI-II mode to the DDI mode will be executed if the ventricular interval is equal to the atrial interval. In another embodiment, the mode switch from the DDI-II mode to the DDD mode will be executed at the occurrence of two consecutive paced ventricular events.

Figure 7:
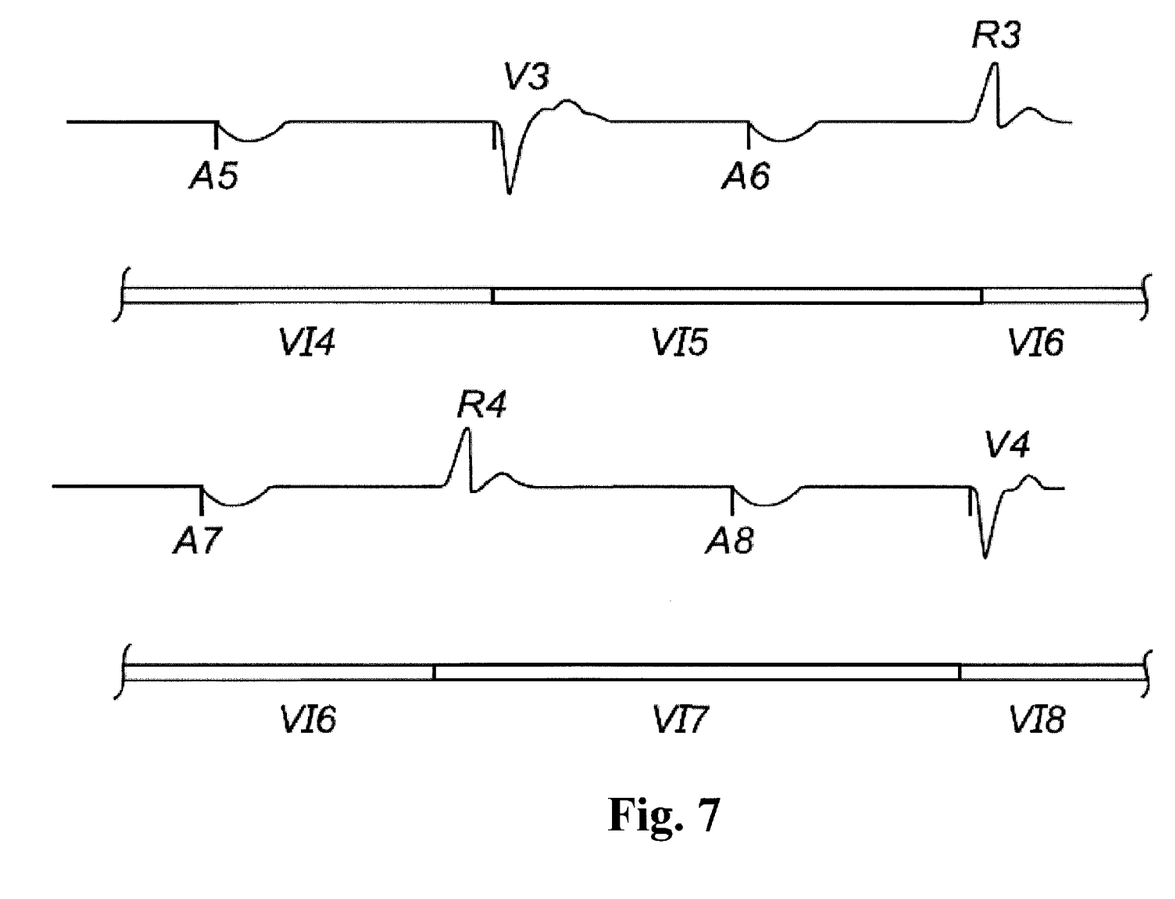
FIG. 7 is a diagram illustrating an example of the cardiac activity and operation of the device during the DDI mode.

Referring now to FIG. 7, an example of the operation in the DDI mode according to the present invention will be discussed.

As discussed above, the DDI mode is an operation mode with a synchronized atrial and ventricular pacing, i.e. sensing and stimulation can be effected in both in atrium and ventricle, in accordance with common practice within the art. An A-V interval timer can be reset by an expired atrial escape interval (atrial pacing is delivered if no inhibition has occurred) and a sensed spontaneous ventricle event outside the A-V interval.

A paced atrial event A5 triggers an atrial refractory interval and an AV interval. The ventricular DDI mode interval VI4 expires without the detection of an intrinsic ventricular event. Synchronized with the point of time at which the ventricular DDI mode interval expires, a stimulation pulse for evoking a ventricular event is delivered resulting in a ventricular event, which is indicated in FIG. 7 with V3. The paced ventricular event V3 triggers a ventricular refractory interval and a new ventricular DDI mode interval VI5. The operational mode is maintained in the DDI mode since the at least one second switching criterion is not satisfied, which in this embodiment is that a predetermined number of consecutive ventricaul pacing pulses have been delivered. In an alternative embodiment, a mode switch from the DDI mode to the DDD mode is performed if the pacemaker has been operated in the DDI mode a predetermined period of time without a restoration of the atrio-ventricular conduction has occurred.

A paced atrial event A6 triggers an atrial refractory interval and an AV interval. An intrinsic ventricular event R3 is detected during the ventricular DDI mode interval VI5, which resets the DDI mode interval VI5 and initiates a new interval VI6. A paced atrial event A7 triggers an atrial refractory interval and an AV interval. An intrinsic ventricular event R4 is detected during the ventricular DDI mode interval VI6, which resets the DDI mode interval VI6 and initiates a new interval VI7. A paced atrial event A8 triggers an atrial refractory interval and an AV interval. The ventricular DDI mode interval VI7 expires without the detection of an intrinsic ventricular event. Synchronized with the point of time at which the ventricular DDI mode interval expires, a stimulation pulse for evoking a ventricular event is delivered, which is indicated in FIG. 7 with V4.

Figure 8:
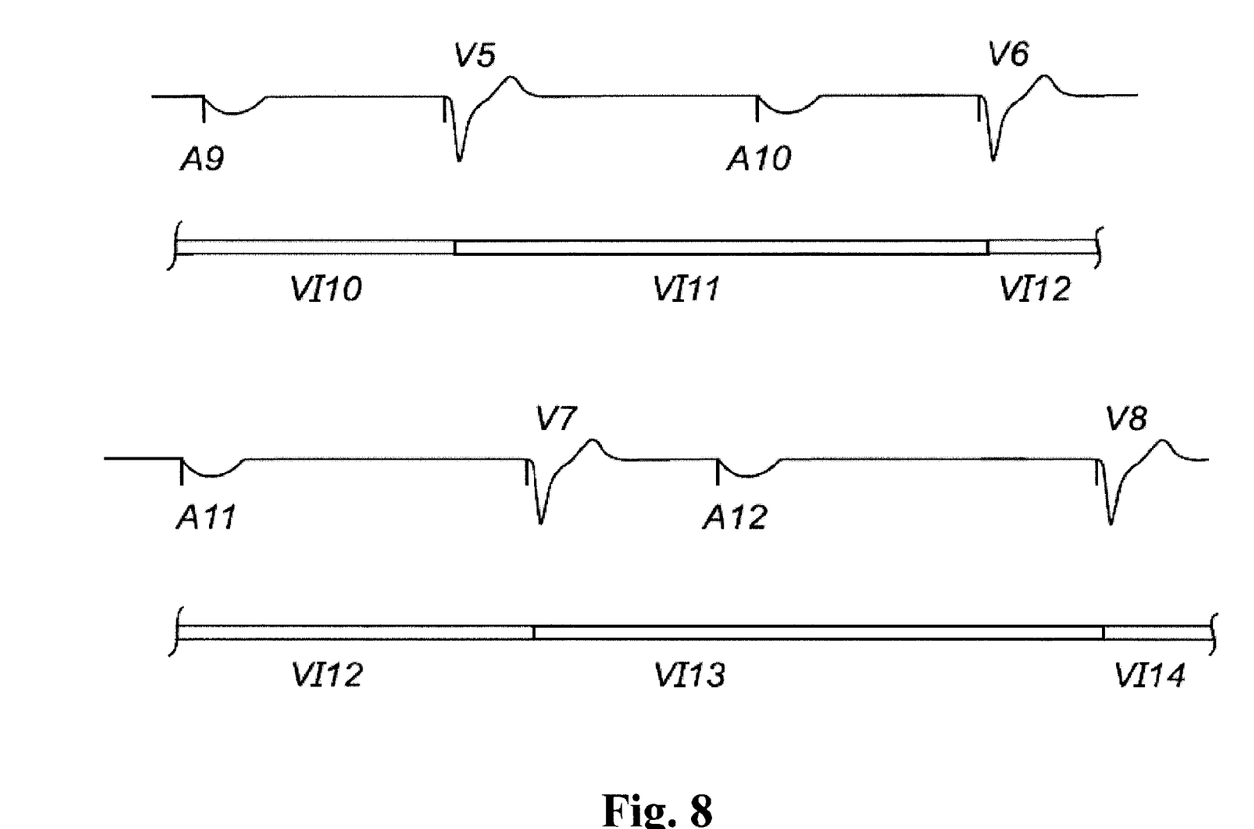
FIG. 8 is a diagram illustrating an example of the cardiac activity and operation of the device during the DDI mode and a mode switch to the DDD mode.

Turning now to FIG. 8, a mode switch from operation in the DDI mode to operation in the DDD mode according to the present invention will be discussed. As discussed above, in the DDD mode, atrial and ventricular events are sensed and stimulation can be delivered in both atrium and ventricle in accordance with common practice within the art. An A-V interval timer can be reset by a sensed atrial event, an expired atrial escape interval and a sensed spontaneous ventricle event outside the A-V interval.

A paced atrial event A9 triggers an atrial refractory interval and an AV interval. A ventricular DDI mode interval VI10 expires without the detection of an intrinsic ventricular event. Synchronized with the point of time at which the ventricular DDI mode interval expires, a stimulation pulse for evoking a ventricular event is delivered, which is indicated in FIG. 8 with V5. The paced ventricular event V5 triggers a ventricular refractory interval and a new ventricular DDD mode interval VI11. A paced atrial event A10 triggers an atrial refractory interval and an AV interval. A ventricular DDD mode interval VI11 expires without the detection of an intrinsic ventricular event. Synchronized with the point of time at which the ventricular DDI mode interval expires, a stimulation pulse for evoking a ventricular event is delivered, which is indicated in FIG. 8 with V6. The paced ventricular event V6 triggers a ventricular refractory interval and a new ventricular DDD mode interval VI12. Further, two consecutive ventricular pacing pulses have been delivered, which, in this embodiment, is the at least one second switching criterion. Thus, the operation mode is switched from the DDI mode to the DDD mode. The operation thus continues in the DDD mode and a paced atrial event A11 triggers an atrial refractory interval and an AV interval. A ventricular DDD mode interval VI12 expires without the detection of an intrinsic ventricular event. Synchronized with the point of time at which the ventricular DDI mode interval expires, a stimulation pulse for evoking a ventricular event is delivered, which is indicated in FIG. 8 with V7. The paced ventricular event V7 triggers a ventricular refractory interval and a new ventricular DDD mode interval VI13. Further, a paced atrial event A12 triggers an atrial refractory interval and an AV interval. According to this embodiment, the ventricular timer returns to the prolonged interval used in the DDD mode for a predetermined number of cycles at regular intervals in order to search for intrinsic events, i.e. R waves. This is illustrated in FIG. 8 by the prolonged ventricular DDD mode interval VI13. As can be seen, no R-wave was detected during this interval and synchronized with the point of time at which the ventricular DDD mode interval expires, a stimulation pulse for evoking a ventricular event is delivered, which is indicated in FIG. 8 with V8. The paced ventricular event V8 triggers a ventricular refractory interval and a new ventricular DDD mode interval VI14, which also is prolonged (not shown in FIG. 8). In this illustrated example, the monitoring period has a length of two cycles but, as the skilled person realizes, may be arbitrary, for example, 3, 4 or 5 cycles. Thus, the ventricular timer will return to the regular DDD ventricular pacing rate from the prolonged ventricular rate after two cycles. In this embodiment, the re-initiating criterion, i.e. the criterion triggering a mode switch back to the DDI-II mode from the DDD mode, is that a predetermined number of consecutive intrinsic ventricular events have been detected, for example, four or five.

Although an exemplary embodiment of the present invention has been shown and described, it will be apparent to those having ordinary skill in the art that a number of changes, modifications, or alterations to the inventions as described herein may be made. For example, during operation in the DDI-II mode, at the occurrence of one paced ventricular event followed by intrinsic ventricular events, the DDI-II mode ventricular pacing rate, which is lower than the base rate of the device, may be increased during a predetermined period of time. If the predetermined period of time, e.g. five cardiac cycles, expires without paced ventricular events, the ventricular pacing rate is adjusted back to the initial rate.

Although modifications and changes may be suggested by those skilled in the art, it is the intention of the inventor to embody within the patent warranted heron all changes and modifications as reasonably and properly come within the scope of his contribution to the art.

I claim as my invention:

1. An implantable medical device comprising:
    a pacing pulse circuit connectable to cardiac leads adapted to deliver cardiac pacing pulses to cardiac tissue via said cardiac leads;
    a monitoring circuit that monitors atrial and/or ventricular events, allowing atrio-ventricular conduction to be detected;
    a switching circuit that switches between operation modes of the implantable medical device including a DDI-II mode, a DDI mode and a DDD mode, said DDI-II mode being an operation mode with an atrial inhibited pacing and a DDI-II mode ventricular pacing rate being lower than a predetermined base rate of the pulse circuit;
    a control circuit configured to:
        operate said device in said DDI-II mode during periods with atrio-ventricular conduction conditions;
        if a block in atrio-ventricular conduction is detected and at least one first switching criterion is satisfied, control said switching circuit to switch from said DDI-II mode to said DDI mode; and
        if a block in atrio-ventricular conduction is detected and at least one second switching criterion is satisfied, control said switching circuit to switch from said DDI mode to said DDD mode; and
        said control circuit being configured to control said switching circuit to switch back to said DDI-II mode at satisfaction of at least one re-initiating criterion in said DDD mode.

2. The implantable medical device according to claim 1, wherein said control circuit is configured to, when said device is operated in said DDI-II mode:

at each intrinsic or paced ventricular event, control said pacing pulse circuit to adapt a ventricular pacing interval according to predetermined rules depending on at least one preceding ventricular event.

3. The implantable medical device according to claim 2, wherein said control circuit is configured to:
at each paced ventricular event, control said pacing pulse circuit to reduce a present ventricular pacing interval with a first predetermined percentage according to said predetermined rules; and
at sensing of at least two consecutive intrinsic ventricular events, control said pacing pulse circuit to prolong said present ventricular pacing interval with a second predetermined percentage according to said predetermined rules.

4. The implantable medical device according to claim 2, wherein said control circuit is configured to:
at each paced ventricular event, control said pacing pulse circuit to reduce a present ventricular pacing interval with a first predetermined percentage in relation to an initial ventricular pacing rate according to said predetermined rules; and
at sensing of at least two consecutive intrinsic ventricular events, control said pacing pulse circuit to prolong said present ventricular pacing interval with a second predetermined percentage in relation to said initial ventricular pacing rate according to said predetermined rules; and
wherein said initial ventricular pacing rate is the DDI-II mode ventricular pacing rate.

5. The implantable medical device according to claim 2, wherein said at least one first switching criterion is that a ventricular pacing interval is at least equal to an atrial pacing interval.

6. The implantable medical device according to claim 1, wherein said at least one first switching criterion is that no atrio-ventricular conduction has been detected during a predetermined second period having a duration of at least two cardiac cycles.

7. The implantable medical device according to claim 1, wherein said atrio-ventricular conduction is periods with consecutive intrinsic ventricular events interrupted by at most a predetermined number of paced ventricular events.

8. The implantable medical device claim 1, wherein said at least one second switching criterion is that ventricular pacing pulses has been delivered for a period having a predetermined length of time or that at least two consecutive ventricular pacing pulses have been delivered.

9. The implantable medical device according claim 1, wherein said control circuit is configured to, when said device operates in said DDI mode, control said switching circuit to switch back to said DDI-II mode if at least one re-initiation criterion for the DDI mode is satisfied.

10. The implantable medical device according to claim 9, wherein said at least one re-initiation criterion for the DDI mode is that atrio-ventricular conduction is restored for a period being longer than a predetermined period of time.

11. The implantable medical device according to claim 9, wherein said at least one re-initiation criterion for the DDI mode is that a predetermined number of consecutive intrinsic ventricular events have been detected.

12. The implantable medical device according claim 1, wherein said reinitiating criterion in said DDD mode is that atrio-ventricular conduction is restored for a period having a duration of a predetermined number of cardiac cycles.

13. The implantable medical device according claim 1, wherein said control circuit is configured to, when said device operates in said DDD mode, regularly search for intrinsic ventricular activity.

14. The implantable medical device according to claim 13, wherein said control circuit is configured to, at predetermined intervals, control said pacing pulse circuit to prolong a present ventricular pacing interval during a period of time having a length of a predetermined number of cycles.

15. The implantable medical device according to claim 14, wherein said control circuit is configured to control said pacing pulse circuit to prolong a present ventricular pacing interval during said period of time to the DDI-II mode ventricular pacing interval.

16. A method for operating an implantable medical device to selectively provide cardiac pacing to a heart of a patient, said method comprising the steps of:
delivering cardiac pacing pulses to cardiac tissue;
detecting atrio-ventricular conduction by monitoring atrial and/or ventricular events;
switching between operation modes of the implantable medical device including a DDI-II mode, a DDI mode and a DDD mode, said DDI-II mode being an operation mode with an atrial inhibited pacing and a DDI-II mode ventricular pacing rate being lower than a predetermined base rate of the pulse circuit,
operating said device in said DDI-II mode during periods with atrio-ventricular conduction conditions;
if a block in atrio-ventricular conduction is detected and at least one first switching criterion is satisfied, switching said DDI-II mode to said DDI mode;
if a block in atrio-ventricular conduction is detected and at least one second switching criterion is satisfied, switching said DDI mode to said DDD mode; and
at satisfaction of at least one re-initiating criterion, switching said DDD mode back to said DDI-II mode.

17. The method according to claim 16, wherein said step of operating said device in said DDI mode comprises:
at each intrinsic or paced ventricular event, adapting a ventricular pacing interval according to predetermined rules depending on at least one preceding ventricular event.

18. The method according to claim 17, wherein said step of adapting comprises the steps of:
at each paced ventricular event, reducing a present ventricular pacing interval with a first predetermined percentage according to said predetermined rules; and
at sensing of at least two consecutive intrinsic ventricular events, prolonging said present ventricular pacing interval with a second predetermined percentage according to said predetermined rules.

19. The method according to claim 17, wherein said step of adapting comprises the steps of:
at each paced ventricular event, reducing a present ventricular pacing interval with a first predetermined percentage in relation to an initial ventricular pacing rate according to said predetermined rules; and
at sensing of at least two consecutive intrinsic ventricular events, prolonging said present ventricular pacing interval with a second predetermined percentage in relation to said initial ventricular pacing rate according to said predetermined rules; and
wherein said initial ventricular pacing rate is the DDI-II mode ventricular pacing rate.

20. The method according to claim 17, wherein said at least one first switching criterion is that a ventricular pacing interval is at least equal to an atrial pacing interval.

21. The method according to claim 16, wherein said at least one first switching criterion is that no atrio-ventricular conduction has been detected during a predetermined second period having a duration of at least two cardiac cycles.

22. The method according to claim 16, wherein said atrio-ventricular conduction is periods with consecutive intrinsic ventricular events interrupted by at most a predetermined number of paced ventricular events.

23. The method according to claim 16, wherein said at least one second switching criterion is that ventricular pacing pulses has been delivered for a period having a predetermined length of time or that at least two consecutive ventricular pacing pulses have been delivered.

24. The method according to claim 16, further comprising the step of, when said device operates in said DDI mode, switching back to said DDI-II mode if at least one re-initiation criterion for the DDI mode is satisfied.

25. The method according to claim 24, wherein said at least one re-initiation criterion for the DDI mode is that atrio-ventricular conduction is restored for a period being longer than a predetermined period of time.

26. The method according to claim 24, wherein said at least one re-initiation criterion for the DDI mode is that a predetermined number of consecutive intrinsic ventricular events have been detected.

27. The method according to claim 16, wherein said re-initiating criterion in said DDD mode is that atrio-ventricular conduction is restored for a period having a duration of a predetermined number of cardiac cycles.

28. The method according to claim 16, further comprising the step of, when said device operates in said DDD mode, regularly searching for intrinsic ventricular activity.

29. The method according to claim 28, wherein the step of searching comprises, at predetermined intervals, prolonging a present ventricular pacing interval during a period of time having a length of a predetermined number of cycles.

30. The method according to claim 29, wherein said step of prolonging comprises prolonging said present ventricular pacing interval to the DDI-II mode ventricular pacing interval during said period of time.

31. A computer-readable medium encoded with programming instructions, said medium being loadable into an internal memory of an implantable medical device comprising a processor and a pulse generator, said processor having access to said internal memory and said programming instructions causing said processor to operate said implantable medical device to:

deliver cardiac pacing pulses to cardiac tissue;

detect atrio-ventricular conduction by monitoring atrial and/or ventricular events;

switch between operation modes of the implantable medical device including a DDI-II mode, a DDI mode and a DDD mode, said DDI-II mode being an operation mode with an atrial inhibited pacing and a DDI-II mode ventricular pacing rate being lower than a predetermined base rate of the pulse circuit, operate said device in said DDI-II mode during periods with atrio-ventricular conduction conditions;

if a block in atrio-ventricular conduction is detected and at least one first switching criterion is satisfied, switch said DDI-II mode to said DDI mode;

if a block in atrio-ventricular conduction is detected and at least one second switching criterion is satisfied, switch said DDI mode to said DDD mode; and satisfaction of at least one re-initiating criterion, switch said DDD mode back to said DDI-II mode.

* * * * *